United States Patent [19]

Koizumi

[11] Patent Number: 4,674,875
[45] Date of Patent: Jun. 23, 1987

[54] METHOD AND APPARATUS FOR INSPECTING SURFACE DEFECTS ON THE MAGNETIC DISK FILE MEMORIES

[75] Inventor: Mitsuyoshi Koizumi, Yokohama, Japan

[73] Assignee: Hitachi, Ltd., Tokyo, Japan

[21] Appl. No.: 679,358

[22] Filed: Dec. 7, 1984

[30] Foreign Application Priority Data

Dec. 9, 1983 [JP] Japan ............................. 58-231362
Sep. 28, 1984 [JP] Japan ............................. 59-201624

[51] Int. Cl.$^4$ ........................................... G01N 21/89
[52] U.S. Cl. .................................. 356/237; 250/563; 250/572
[58] Field of Search ..................... 356/237, 445, 446; 250/562, 563, 572

[56] References Cited

U.S. PATENT DOCUMENTS 3,734,626 5/1973 Roberts et al. ..................... 356/371
4,395,122 7/1983 Southgate et al. .
4,423,331 12/1983 Koizumi et al. .

Primary Examiner—Davis L. Willis
Assistant Examiner—Matthew W. Koren
Attorney, Agent, or Firm—Antonelli, Terry & Wands

[57] ABSTRACT

Method and apparatus for inspecting surface defects of a sample in which oblique illumination is applied onto a surface of the sample and in which illuminance of reflected beams generated from the surface is measured. Shading plate having double pinholes or double slits is used as means for shading a scattered beam from aventurine prominences of the sample surface to fully shade the scattered beam so that the inspection is accurately executed.

19 Claims, 31 Drawing Figures

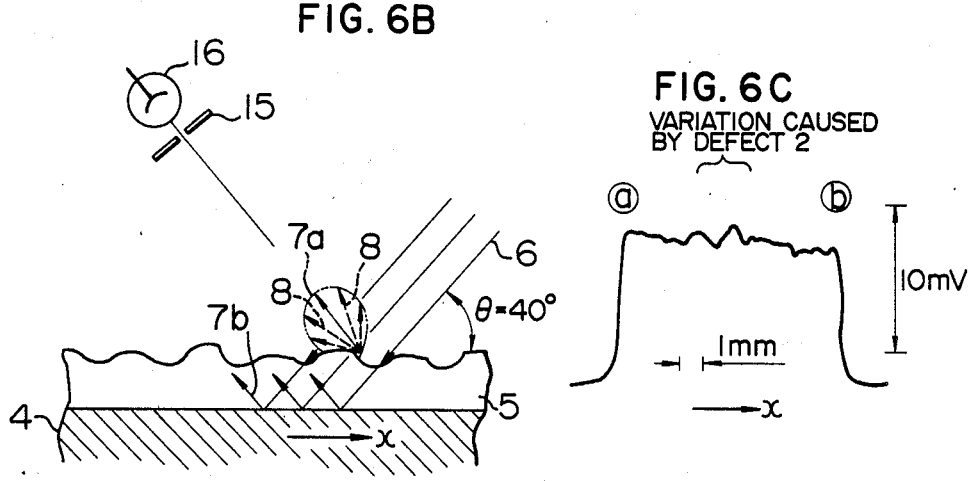
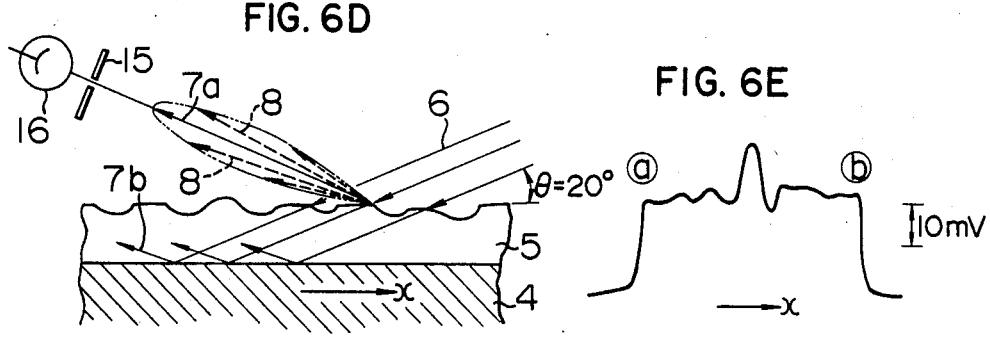
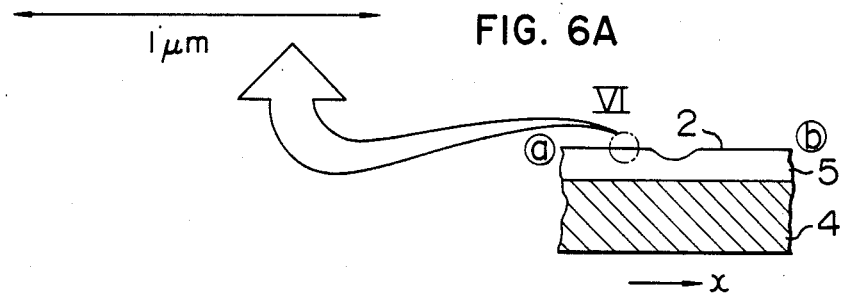

SIGNAL VARIATION CAUSED BY DEFECT

METHOD AND APPARATUS FOR INSPECTING SURFACE DEFECTS ON THE MAGNETIC DISK FILE MEMORIES

BACKGROUND OF THE INVENTION

1. Field of the Invention

The present invention relates to a method and an apparatus for inspecting surface defects on the magnetic disk file memories and in particular to a method and an apparatus for inspecting surface defects of magnetic disks, whereby defects present on the surface of the magnetic disk having minute aventurine prominences and dents can be automatically inspected.

2. Description of the Prior Art

A magnetic disk is obtained by applying magnetic oxidized steel grains onto a polished and finished aluminium surface. In the application process, a mixture liquid composed of a solvent and oxidized steel grains is dropped onto an aluminium plate rotating at high speed and thereafter the solvent is evaporated. On the film thus formed in the application process, craterlike defects and stripe defects are caused.

This phenomenon will now be described in detail by referring to the following drawings.

FIG. 1 is a plan view of a magnetic disk. FIG. 2 is an enlarged oblique view of a portion II cut away from the disk illustrated in FIG. 1. FIG. 3 is an enlarged oblique view of a portion III cut away from the disk illustrated in FIG. 1, FIG. 4 is an enlarged sectional view of a typical defect appearing on the magnetic disk.

In those figures, reference numeral 1 denotes a magnetic disk having a film layer 5 formed by applying magnetic oxidized steel grains onto an aluminium plane 4 thereof. Reference numerals 2 and 3 respectively denote a craterlike defect and a stripe defect caused on the film layer 5. If a portion of the aluminium plane 4 where it contacts with the mixture liquid is not pure, the craterlike defect 2 appears on the surface of the film layer 5 after the solvent has been evaporated. If the grain density is not uniform somewhere, the stripe defect 3 is caused on a radially outer end of the aluminium plane 4 by the centrifugal force due to rotation caused by spinner.

Since the craterlike defect 2 and the stripe defect 3 might cause a read/write error of the magnetic disk file memory 1, it is necessary to effect inspection to see whether such a defect exists or not after the application process has been completed.

The aluminium plane 4 is 2 mm in thickness and the film layer 5 formed on the plane 4 is 1 $\mu$m in thickness. The film layer 5 has minute aventurine dents and prominences which are 0.01 $\mu$mRa in surface roughness. The size of the craterlike defect 2 and the width of the stripe defect 3 (hereafter collectively referred to as size d) are typically 0.5 to 2 mm as illustrated in FIG. 4. Since a defect more than 0.2 $\mu$m in depth h might cause a read write error, the depth h of a defect more than 0.2 $\mu$m must be detected. Accordingly, the depth h of a defect to be detected is extremely small in relation to the size d as represented by the ratio as $$h/d = 1:2500 \ (\sim 10,000).$$

Such a small defect can be detected by using interference fringes such as Newton's rings, for example, if the surface is optically smooth. However, the Newton's rings cannot be applied to the surface having minute aventurine dents and prominences such as the surface of the magnetic disk file memories. Such a surface has heretofore been visually inspected, resulting in the low reliability of the magnetic disk performance if a human inspector missed the defects.

SUMMARY OF THE INVENTION

An object of the present invention is to provide a method and an apparatus for inspecting defects on the surface of a magnetic disk, whereby the above described drawbacks of the prior art are overcome and it is permitted to automatically detect a defect which has appeared on the surface of a magnetic disk having minute aventurine dents and prominences and which has a depth significantly smaller than the size of the dents and prominences.

In accordance with the present invention, the method for inspecting surface defects of magnetic disks includes (a) applying parallel (coherent in space) oblique illumination beams onto a surface of a magnetic disk at an oblique angle, (b) measuring the illuminance distribution of reflected beams generated from said surface by using photoelectric transducer means having straylight-stop optical means, scattered beams being cut off by said optical means; and (c) detecting defects distributed over said surface having minute aventurine dents and prominences based upon said measured illuminance distribution, each of said defects having a depth significantly smaller than its size.

In accordance with the present invention, the apparatus for inspecting surface defects of magnetic disks includes: (a) a parallel (coherent) oblique illumination unit; (b) a photoelectric transducer unit having a straylight-stop optical system, scattered beams being cut off by said stray-light-stop optical system; and (c) a sample feeding stage.

BRIEF DESCRIPTION OF THE DRAWINGS

FIGS. 5A to 9C are drawings for illustrating the basic facts relating to the present invention.

FIGS. 5A and 5B illustrate illuminance distributions of reflected beams generated from the surface of the magnetic disk from two effects caused by defects.

FIGS. 6A to 6E are enlarged sectional views near the surface of the magnetic disk and illuminance distribution diagrams of reflected beams for indicating the influence of the oblique angle of the parallel (coherent) oblique illumination beams upon the constrast of illuminance distribution of the reflected beams.

FIGS. 9A to 9C are drawings illustrating means for eliminating the influence of scattered beams, which illustrate a photoelectric transducer unit having another stray-light-stop optical system and illustrate illuminance distribution of reflected beams corresponding to a craterlike defect measured by using the photoelectric transducer unit.

DESCRIPTION OF THE PREFERRED EMBODIMENT

Prior to proceeding to the description of the embodiment, basic facts relating to the present invention will be described.

By applying parallel (coherent) oblique illumination beams onto the surface of a magnetic disk and measuring the distribution of illuminance of the beams reflected by the surface, defects existing on the surface are detected.

The present inventor found that a phenomenon occurs when there exists some defects on a surface: (a) a concave mirror effect due to the defect, and (b) an attenuation effect exercised upon the beam reflected by the surface of the aluminium plane, cause multiplicatively variation in the distribution of illuminance. This phenomenon is effectively used in the present invention. In measuring the illuminance distribution of the reflected beams, the scattered light supplied from the surface of the magnetic disk must be cut off by a straylight-stop optical system to magnify the contrast of the variation in illuminance, resulting in stable detection.

In detecting a stripe defect, a cylindrical lens is used and the image of the defect is compressed in the lengthwise direction of the stripe defect to magnify the contrast of variation in illuminance.

Figure 1:
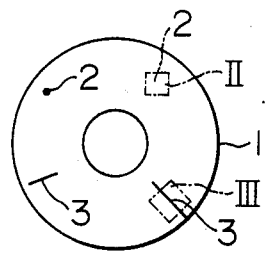
FIG. 1 is a plan view of a magnetic disk.
Figure 2:
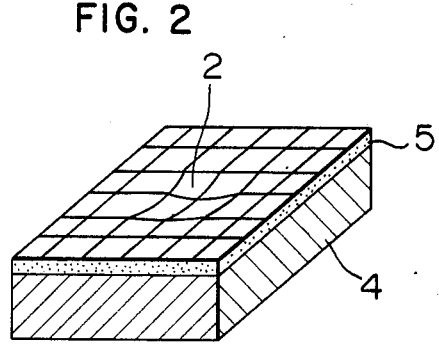
FIG. 2 is an enlarged oblique view of a portion II cut away from the disk illustrated in FIG. 1.
Figure 3:
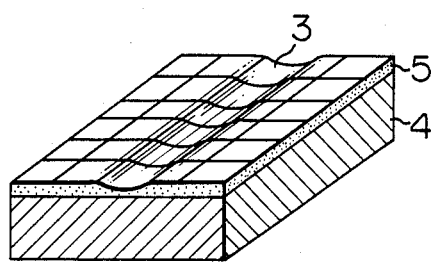
FIG. 3 is an enlarged oblique view of a portion III cut away from the disk illustrated in FIG. 1.
Figure 4:
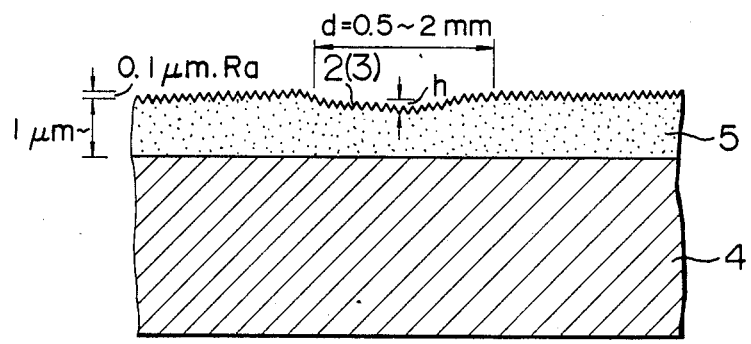
FIG. 4 is an enlarged sectional view of a typical defect appearing on the magnetic disk.
Figure 5A:
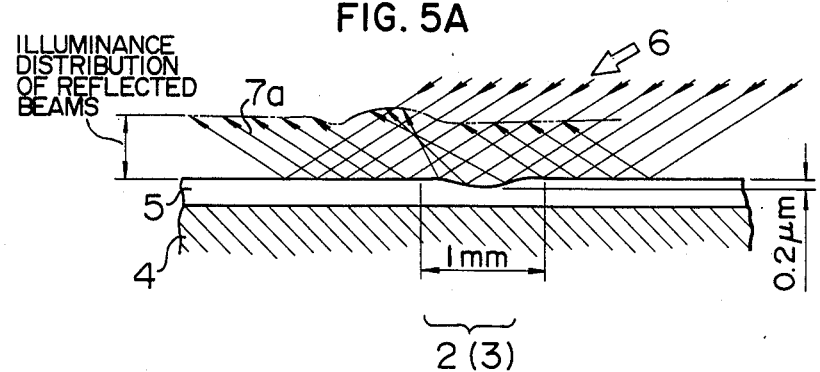
Figure 10A:
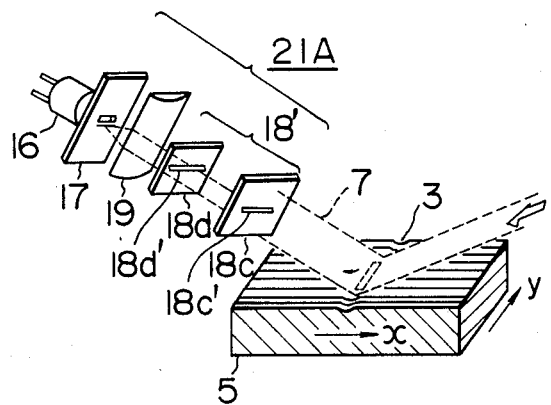
FIGS. 10A to 10D are drawings illustrating means for detecting stripe defects, which illustrate a photoelectric transducer units having two different type straylight-stop optical systems, and illuminance distributions of reflected beams corresponding to a stripe defect measured by those photoelectric transducer units.
Figure 10B:
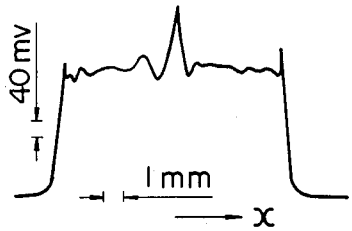
Figure 10C:
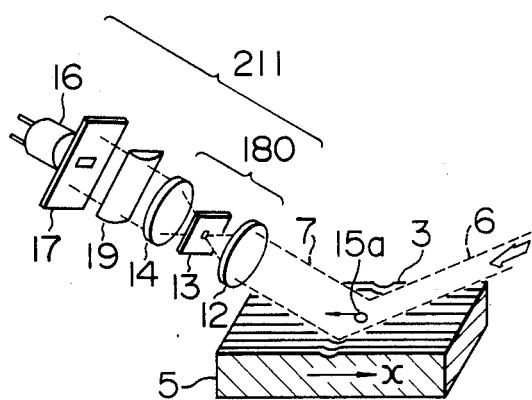
Figure 10D:
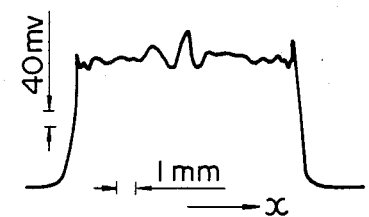
Figure 11:
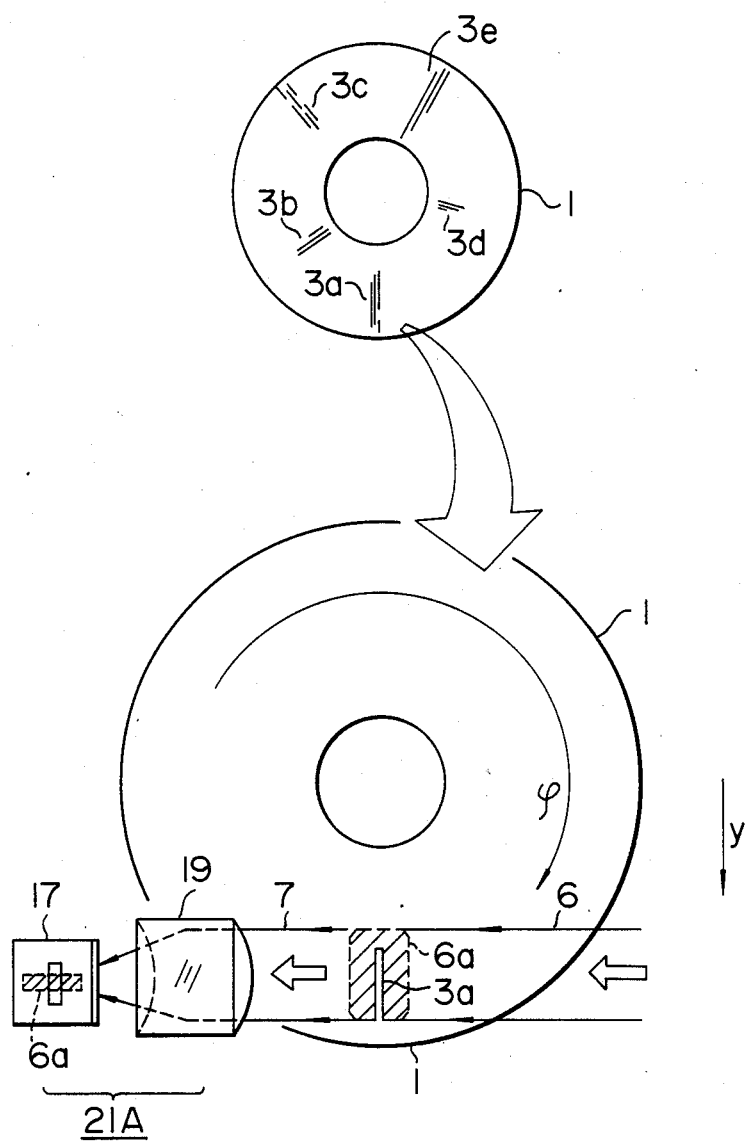
FIG. 11 is a plan view for illustrating the state when stripe defects are being detected by using the photoelectric transducer unit having the cylindrical lens illustrated in FIG. 8A.

FIGS. 5A to 8D and 11 are drawings for illustrating the basic facts relating to the present invention. FIGS. 5A and 5B illustrate illuminance distributions of reflected beams generated from the surface of the magnetic disk from two effects caused by defects. FIGS. 6A to 6E are enlarged sectional views on the surface of the magnetic disk and illuminance distribution diagrams for indicating the influence of the oblique angle of the parallel (coherent) oblique illumination beams upon the constrast of illuminance distribution of the reflected beams. FIGS. 7A to 7C are drawings illustrating means for eliminating the influence of scattered beams, which illustrate a photoelectric transducer unit having a straylight-stop optical system and illustrate illuminance distributions of reflected beams corresponding to craterlike defects measured by means of the photoelectric transducer unit. FIGS. 8A to 8D are drawings illustrating means for detecting stripe defects, which illustrate a photoelectric transducer unit (a) having a cylindrical lens and a slit, a photoelectric transducer unit, (b) having no cylindrical lens, and illuminance distributions of reflected beams corresponding to stripe defects measured by those photoelectric transducer units. FIGS. 9A to 10D are drawings illustrating other embodiments corresponding to FIGS. 7A to 8D. FIG. 11 is a plan view for illustrating the state when stripe defects are being detected by using the photoelectric transducer unit having a cylindrical lens illustrated in FIG. 8A.

In those figures, reference numerals 2 and 3 denote a craterlike defect and a stripe defect, respectively. Reference numerals 4 and 5 denote an aluminium plane and a film layer formed on the plane, respectively. Like reference numerals refer to like parts.

Figure 5B:
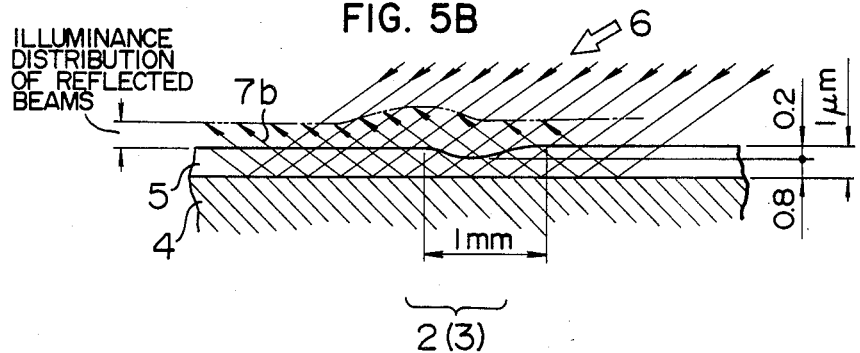

FIG. 5A illustrates the concave mirror effect caused by a defect. When parallel (coherent) oblique illumination beams 6 are hit upon to the film layer 5, the illuminance distribution of beams 7a reflected by the film surface varies locally as illustrated in FIG. 5A by the concave mirror effect of the defect 2(3). This is the concave mirror effect (a) due to the defect. FIG. 5B illustrates the attenuation effect caused by the layer film 5 on the surface of the disk. Since the film layer 5 having a thickness of 1 $\mu$m is semitransparent, the parallel (coherent) oblique beams 6 are reflected at the surface of the aluminium plane 4 to form reflected beams 7b from the aluminium surface. The parallel coherent oblique illumination beams 6 transmitted through the defect 2(3), and then the beams reflected by the surface of the aluminium are provided with less attenuation in the film layer 5 as compared with normal thickness portions excepting the defect 2(3). Accordingly, a local variation appears in the illuminance distribution of the beams 7b reflected by the aluminium surface. This is the attenuation effect (b) exercised upon the beam reflected by the surface of the aluminium plane naturally. These effects are occurred by the concave or convex defect.

A variation in the illuminance distribution produced by the defect and by the multiplicative effects (a) and (b) is utilized in the present invention.

Effects caused by a oblique angle $\theta$ of the parallel coherent oblique illumination beams will not be described by referring to FIGS. 6A to 6E.

FIG. 6A shows a region extending from point ⓐ to point ⓑ around a defect. FIG. 6B is an enlarged sectional view of a portion VI illustrated in FIG. 6A when parallel (coherent) oblique illumination beams 6 are applied to the portion VI at a oblique angle $\theta = 40°$. FIG. 6C shows the illuminance distribution of the reflected beams in the region extending from ⓐ to ⓑ around the defect when the oblique angle $\theta = 40°$. And FIG. 6D is an enlarged sectional view of the portion VI illustrated in FIG. 6A when parallel oblique illumination beams 6 are applied to the portion VI at a oblique angle $\theta = 20°$. FIG. 6E shows the illuminance distribution of the reflected beams in the region extending from a to b around the defect when the oblique angle $\theta = 20°$.

Since the surface of the film layer 5 has minute aventurine dents and prominences, reflected beams 7a and scattered beams 8 are produced from the parallel (coherent) oblique illumination beams 6. The reflected beams 7a and the scattered beams 8 are produced respectively at the flat portions and edge portions of the minute aventurine dents and prominences. As the oblique angle $\theta$ is decreased, the apparent ratio of the flat portions to the edge portions becomes large, the illuminance of the reflected beams 7a being raised. The present inventor measured the illuminance distribution of reflected beams over a region from ⓐ to ⓑ by using a pinhole 15 and a photoelectric transducer element 16, while a sample magnetic disk is being moved in the x direction. The angle $\theta$ was chosen to be 20° or 40°. As illustrated in FIGS. 6C and 6E, it was found that the intensity distribution illuminance of the reflected beams for $\theta = 20°$ is approximately five times larger than that for $\theta = 40°$ and the variation in illuminance (contrast) for $\theta = 20°$ is also larger than that for $\theta = 40°$. Accordingly, it is desirable for the oblique angle $\theta$ of the parallel oblique illumination beams 6 to be small.

A method for removing the effect of the scattered beams will now be described by referring to FIGS. 7A to 7C.

Figure 7A:
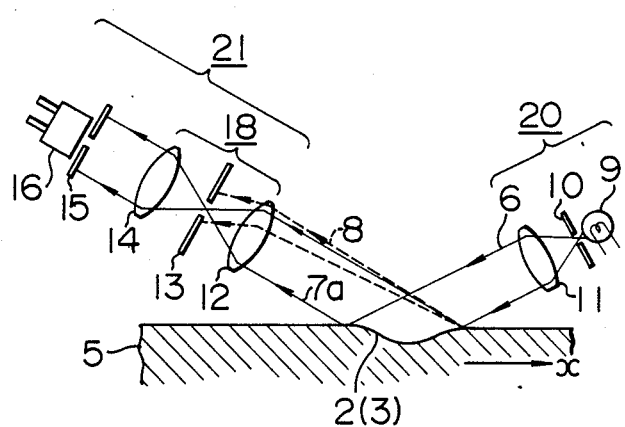
FIGS. 7A to 7C are drawings illustrating means for eliminating the influence of scattered beams, which illustrate a photoelectric transducer unit having a straylight-stop optical system and illustrate illuminance distributions of reflected beams corresponding to craterlike defects measured by using the photoelectric transducer unit.

FIG. 7A schematically shows a parallel (coherent) oblique illumination unit 20 and a photoelectric transducer unit 21 including a stray-light-stop optical system 18. FIG. 7B shows the illuminance distribution of the reflected beams corresponding to the craterlike defect, which is measured by using the photoelectric transducer unit 21 illustrated in FIG. 7A. FIG. 7C shows the illuminance distribution of the reflected beams corresponding to the craterlike defect, which is measured without using the stray-light-stop optical system 18 illustrated in FIG. 7A.

The above described parallel (coherent) oblique illumination unit 20 is composed of a light source 9 (laser light is preferable), a pinhole 10 and a convex lens 11. The photoelectric transducer unit 21 is composed of the stray-light-stop optical system 18, a pinhole 15, and a photoelectric transducer element 16. The stray-light-stop optical system 18 is composed of two convex lenses 12 and 14 and a pinhole 13 set between the lenses. And the opening circle of the pinhole 13 coincides with the focal point of the convex lens 12. Accordingly, the reflected beam 7a passes through the opening. However, the scattered beam 8 is cut off. After passing through the opening, the reflected beam 7a are converted into parallel beams again by the convex lens 14 and pass through the pinhole 15 to the photoelectric transducer element 16 to measure the illuminance distribution of the reflected beams.

Figure 7B:
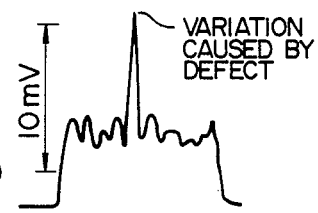
Figure 7C:
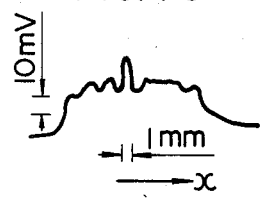

The contrast of the illuminance distribution of the reflected beams measured by using the photoelectric transducer unit 21 which is equipped with the stray-light-stop optical system 18 is illustrated in FIG. 7B. On the other hand, the contrast of the illuminance distribution of the reflected beams measured by using the photoelectric transducer unit which is not equipped with the stray-light-stop optical system 18, i.e., the photoelectric transducer unit 21 apart from the stray-light-stop optical system 18 is illustrated in FIG. 7C. In the absence of the stray-light-stop optical systems 18, the variation in illuminance is small, therefore stable detection being not attained. Meanwhile, in the presence of the optical system 18, the illuminance variation (contrast) corresponding to the craterlike defect 2 becomes significantly high.

Finally, a method for detecting the stripe defect 3 will now be described by referring to FIGS. 8A to 8D and FIG. 11.

Figure 8A:
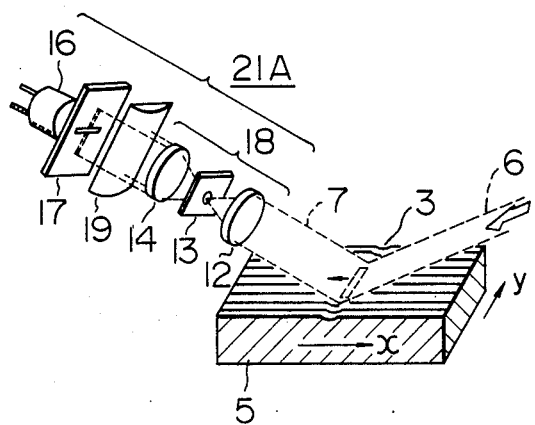
FIGS. 8A to 8D are drawings illustrating means for detecting stripe defects, which illustrate (a) a photoelectric transducer unit having a cylindrical lens, (b) a photoelectric transducer unit having no cylindrical lenses, and illuminance distributions of reflected beams corresponding to stripe defects measured by those photoelectric transducer units.
Figure 8B:
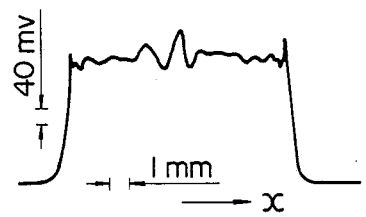
Figure 8C:
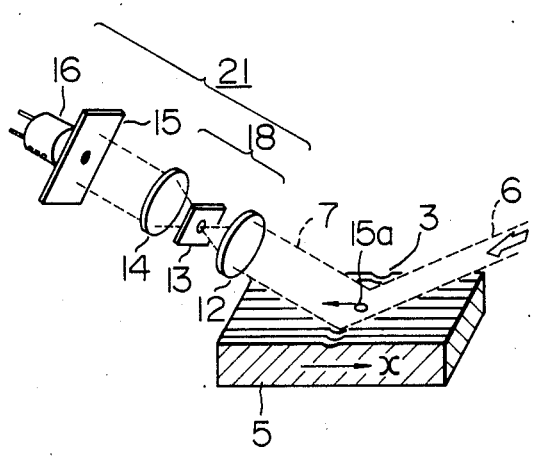
Figure 8D:
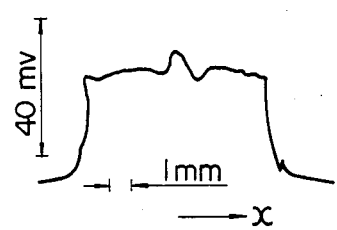

FIG. 8A schematically shows the photoelectric transducer unit 21A which includes a cylindrical lens 19 and which is used for detecting the stripe defect 3. FIG. 8B shows the illuminance distribution of the reflected beams corresponding to the stripe defect 3, measured by using the photoelectric transducer unit 21A illustrated in FIG. 8A. FIG. 8C schematically shows the photoelectric transducer unit 21 illustrated in FIG. 7A, i.e., the photoelectric transducer unit without the cylindrical lens 19 equipped. FIG. 8D shows the illuminance distribution of the reflected beams corresponding to the stripe defect, measured by using the photoelectric transducer unit 21 illustrated in FIG. 8C.

The cylindrical lens 19 effects optical compression only in the lengthwise direction of the stripe defect 3. Behind the cylindrical lens 19, a slit 17 having a narrow width in a direction parallel to the above described compression direction is disposed. As illustrated in FIG. 8B, scanning by using the photoelectric transducer unit 21A including the cylindrical lens 19 and the slit 17 produces a high contrast in illuminance corresponding to the defect 3 as compared with the photoelectric transducer unit 21 without cylindrical lens 19. The lengthwise direction of the stripe defect 3 coincides with the radial direction of the magnetic disk 1. By rotating the magnetic disk 1 in the $\rho$ direction as illustrated in FIG. 11, therefore, stripe defects 3a, 3c and 3d are detected by the photoelectric transducer unit 21A. For detection of the stripe defects 3b and 3d located at the center side of the magnetic disk 1, the magnetic disk 1 is translated by an appropriate distance in the y direction from the position shown in FIG. 11, and then the magnetic disk 1 is rotated. Thus, the parallel (coherent) oblique illumination portion 6a is displaced to the center side of the disk, and the stripe defects 3b and 3d are similarly detected.

Another embodiment of the present invention will now be described by referring to FIGS. 9A to 10D.

At first, an another method for eliminating the effect of the scattered beams will be described by referring to FIGS. 9A to 9C.

Figure 9A:
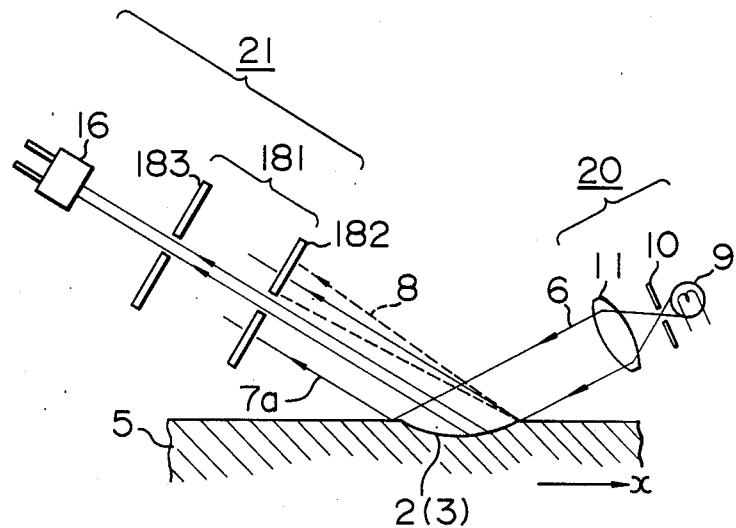

FIG. 9A schematically shows a parallel coherent oblique illumination unit 20 and a photoelectric transducer unit 21 including a stray-light-stop optical system 181. FIG. 9B shows the illuminance distribution of the reflected beams corresponding to the craterlike defect, which is measured by using the photoelectric transducer unit 21 illustrated in FIG. 9A. FIG. 9C shows the illuminance distribution of the reflected beams corresponding to the craterlike defect, which is measured without using the optical system unit 181 illustrated in FIG. 9A.

The above described parallel coherent oblique illumination unit 20 is composed of a light source 9, a pinhole 10, and a convex lens 11. The photoelectric transducer unit 21 is composed of a photoelectric transducer element 16 and a stray-light-stop optical system 181 including two pinholes 182 and 183. Among reflected beams 7a, only parallel coherent beams located at the central parts are passed through the two pinholes 182 and 183 and applied to the photoelectric transducer element 16 to measure the distribution of the reflected beams.

Figure 9B:
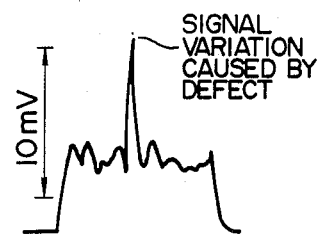
Figure 9C:
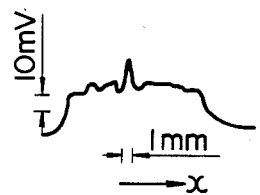

The contrast of the illuminance distribution of the reflected beams measured by using the photoelectric transducer unit 21 which is equipped with the stray-light-stop optical system 181 is illustrated in FIG. 9B. On the other hand, the contrast of the illuminance distribution of the reflected beams measured by using the photoelectric transducer unit which is not equipped with the stray-light-stop optical system 181, i.e., the photoelectric transducer unit 21 appart from the stray-light-stop optical system 181 is illustrated in FIG. 9C. In the absence of the stray-light-stop optical system 181, the variation in illuminance is small, therefore stable detection being not attained. Meanwhile, in the presence of the stray-light-stop optical system 181, the illuminance variation (contrast) corresponding to the craterlike defect 2 becomes significantly large.

Finally, a method for detecting the stripe defect 3 will now be described by referring to FIGS. 10A to 10D.

FIG. 10A schematically shows the photoelectric transducer unit 21A which includes a cylindrical lens 19 and which is used for detecting the stripe defect 3. FIG. 10B shows the illuminance distribution of the reflected beams corresponding to the stripe defect 3, measured by using the photoelectric transducer unit 21A illustrated in FIG. 10A.

FIG. 10C schematically shows the photoelectric transducer unit 211 which includes stray-light-stop optical system 180. FIG. 10D shows the illuminance distribution of the reflected beams corresponding to the stripe defect 3, measured by using the photoelectric transducer unit 211 illustrated in FIG. 10C. (Signal shown in FIG. 10D is same as the signal shown in FIG. 8B.)

Comparing FIG. 10B and FIG. 10D, contrast in signal shown in FIG. 10B is higher than contrast in signal shown in FIG. 10D. This is because flare produced by convex lens 12 or 14 degrades the signal obtained by the photoelectric transducer unit 211 as shown in FIG. 10D.

The present invention is based upon findings heretofore described. The present invention will now be described by referring to embodiments.

Figure 12:
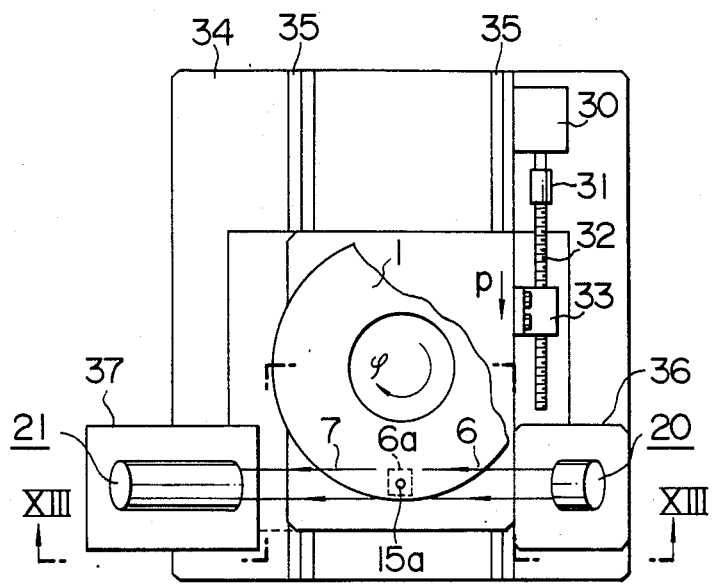
FIG. 12 is a plan view of an example of a surface defect inspection unit used to carry into effect an embodiment of a surface defect inspection method for magnetic disks according to the present invention.
Figure 13:
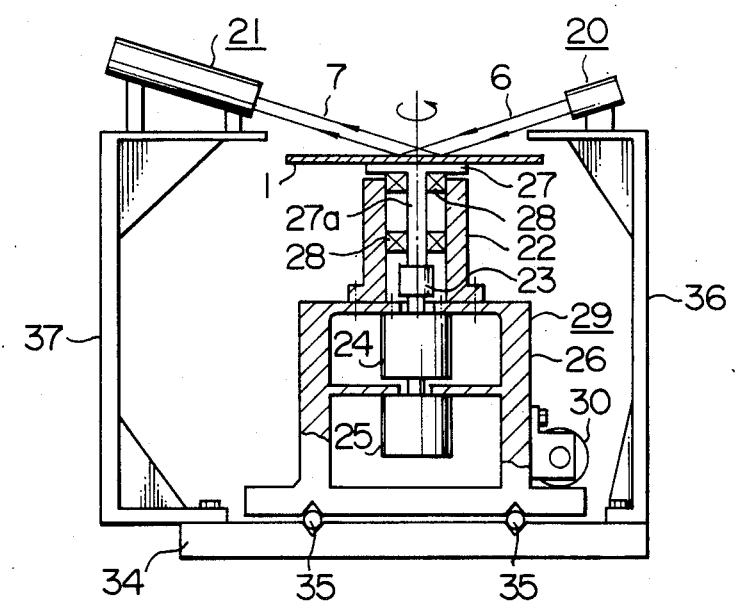
FIG. 13 is a sectional view along a line XI—XI illustrated in FIG. 12.
Figure 14:
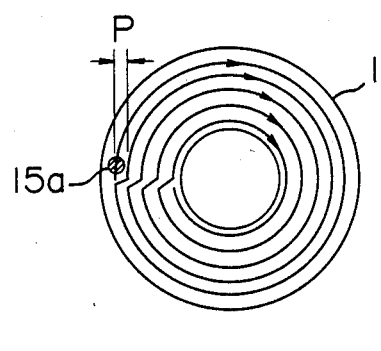
FIG. 14 is a plan view for illustrating a scanning method used in inspecting craterlike defects.
Figure 15:
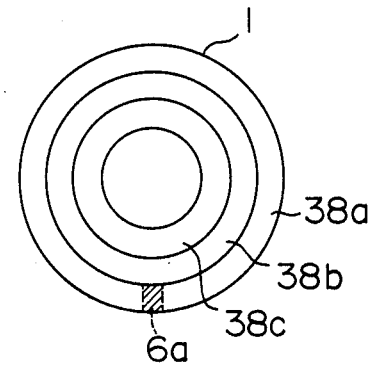
FIG. 15 is a plan view for illustrating a scanning method used in inspecting stripe defects.
Figure 16:
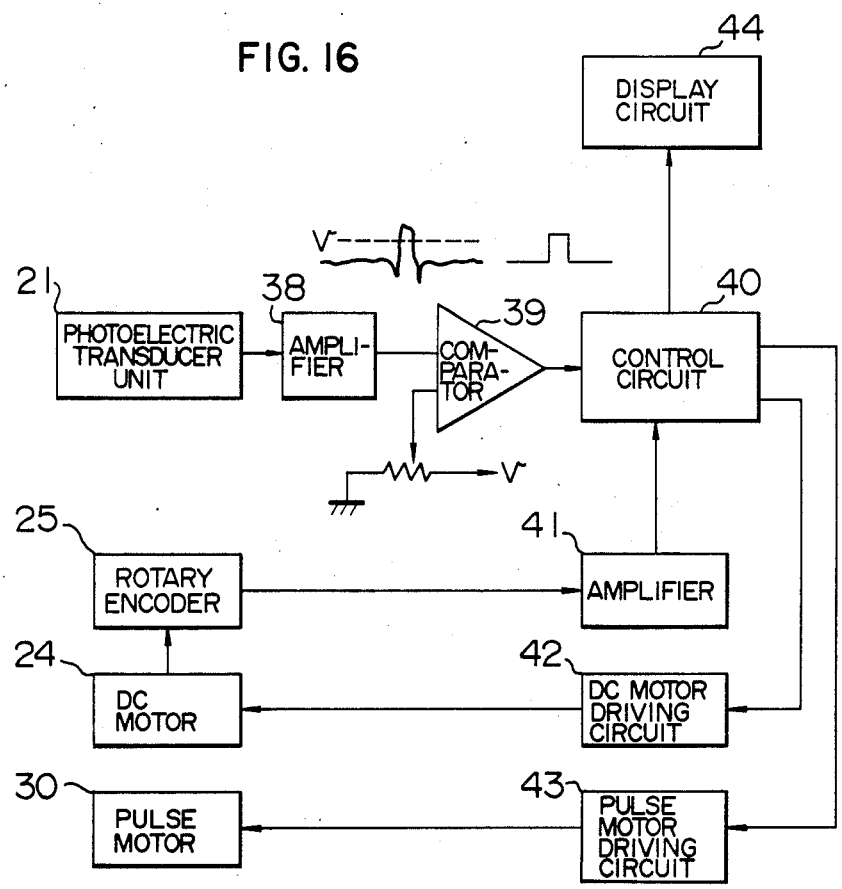
FIG. 16 is an inspection block diagram for illustrating the operation of the surface defect inspection processing unit for magnetic disk illustrated in FIG. 12.

FIG. 12 is a plan view of an example of a surface defect inspection unit used to carry into effect an embodiment of a surface defect inspection method for magnetic disks according to the present invention. FIG. 13 is a sectional view along a line XI—XI illustrated in FIG. 12. FIG. 14 is a plan view for illustrating a scanning method used in inspecting craterlike defects. FIG. 15 is a plan view for illustrating a scanning method used in inspecting stripe defects. FIG. 16 is an inspection block diagram for illustrating the operation of the surface defect inspection processing unit for magnetic disk illustrated in FIG. 12.

In FIGS. 12 and 13, a being inspected magnetic disk 1 is mounted on a holder 27. A rotation axis 27a of the holder 27 is supported by bearing 28. An end of the rotation axis 27a is coupled to a DC motor 24 via a coupling 23. The other axis of the DC motor 24 is connected to an rotary encoder 25. These components are mounted on housings 22 and 26 to form a sample feeding stage 29. The sample feeding stage 29 is so mounted on a base 34 via bearing 35 as to be movable in a direction P(g). A pulse motor 30 mounted on the base 34 can translate the sample feeding stage 29 mounted on the bearing 35 (in the P direction) via a coupling 31, a male screw 32, and a female screw 33 attached to the housing 26.

A parallel coherent oblique illumination unit 20 applies parallel coherent oblique illumination beams 6 onto the surface of a magnetic disk 1 at an oblique angle and is composed of the light source 9, the pinhole 10, and the convex lens 11 as illustrated in FIG. 7A. The parallel coherent oblique illumination unit 20 is mounted on a prop 36 which is erected on the base 34. A photoelectric transducer unit 21 includes the pinhole 15 and the photoelectric transducer element 16 located behind the stray-light-stop optical system 18 as illustrated in FIG. 7A. The stray-light-stop optical system 18 includes two convex lenses 12 and 14 and the pinhole 13 inserted between those lenses. The photoelectric transducer unit 21 is so mounted on a prop 37 erected on the base 34 as to measure the illuminance of the reflected beams 7 (including 7a and 7b) which are produced by reflection of the parallel coherent oblique illumination beams 6 at the surface of the magnetic disk 1.

Operation for detecting the craterlike defect by using the surface defect inspection unit thus constituted for a magnetic disk will now be described as follows.

The magnetic disk 1 is placed on the holder 27 and fixed thereto. When the surface defect inspection unit is turned ON, parallel coherent oblique illumination beams 6 emitted from the parallel coherent oblique illumination unit 20 are applied onto the surface of the magnetic disk 1. The pulse motor 30 and the DC motor 24 are driven. A craterlike defect on the magnetic disk 1 is detected in the photoelectric transducer unit 21 by combining the translation P having a distance and a pitch p with the rotation ρ. The distance of the pitch P is equal to the size of a portion 15a on the magnetic disk 1 which corresponds to the opening of the pinhole 15. And the position of the defect is indicated by a display circuit 44.

This operation will now be described by referring to the inspection block diagram of FIG. 16. A detection signal fed from the photoelectric transducer unit 21 is supplied to a comparator 39 via an amplifier 38. In the comparator 39, the detection signal is compared with the reference voltage V to send a binary signal to a control circuit 40. The control circuit 40 activates a DC motor drive circuit 42 and a pulse motor driving circuit 43 to drive the DC motor 24 and the pulse motor 30, respectively. The position of the magnetic disk 1 in the rotation direction detected by an rotary encoder 25 is supplied to the control circuits 40 via an amplifier 41. Thus, the position of the defect on the magnetic disk is displayed by the display circuit 44, as described before. After the pinhole scanning for the entire surface of the magnetic disk 1 has been completed, the surface defect inspection unit for magnetic disk is turned OFF.

Operation for detecting a stripe defect will now be described as follows.

In this case, the photoelectric transducer unit 21A having the cylindrical lens 19 as illustrated in FIG. 8A is mounted on the prop 37 in the photoelectric transducer unit 21A. As illustrated in FIG. 15, scanning may be conducted by successively scanning ring zones 38a, 38b and 38c, each of which has a width of the parallel coherent oblique illumination portion 6a as illustrated in FIG. 15.

By using the above described embodiments, it becomes possible to inspect the craterlike defect 2 and the stripe defect 3 existing on the film layer 5 of the magnetic disk 1 automatically and accurately. The reliability of the magnetic disk 1 performance can thus be significantly improved.

In the above described embodiments, stripe defects must be inspected by using the photoelectric transducer unit 21A which is different from the photoelectric transducer unit 21 used for inspecting craterlike defects. However, craterlike defects and stripe defects can be simultaneously inspected by using alternative configuration. In a photoelectric transducer unit having that alternative configuration, a semitransparent mirror is disposed behind the stray-light-stop optical system 18 to split the light path of the reflected beam. In one light path, the pinhole 15 and the photoelectric transducer unit 16 are disposed. In the other light path, the cylindrical lens 19, the slit 17, and the photoelectric transducer element 16 are disposed.

The above described surface defect inspection method and apparatus can be applied not only to detection of surface defects of the magnetic disk 1 but also to detection of surface defects on other planes having minute averturine dents and prominences such as LSI wafer surfaces, and etcs.

As heretofore described in detail, the present invention provides a method and an apparatus for inspecting defects on the surface of a magnetic disk, whereby it is permitted to automatically detect a defect which has appeared on the surface of a magnetic disk having minute averturine dents and prominences and which has a depth or height extremely smaller than the size.

I claim:

1. A method for inspecting surface defects of magnetic disks comprising:

applying parallel coherent in space oblique illumination beams onto a surface of a plate at a oblique angle;

measuring the illuminance distribution of reflected beams generated from said surface by using photoelectric transducer means having stray-light-stop optical means, scattered beams being cut off by said stray-light-stop optical means, said photoelectric transducer means including a photoelectric transducer element and at least two plates, each plate having an aperture therein and arranged for introducing the reflected beams to said photoelectric transducer element; and detecting defects distributed over said surface having minute averturine dents and prominences based upon said measured illuminance distribution, each of said defects having a depth (or height) significantly smaller than its size.

2. A method for inspecting surface defects of magnetic disks according to claim 1, wherein said photoelectric transducer means includes said photoelectric transducer element and one of said plates with said aperture being a pinhole and arranged behind said stray-light-stop optical means and wherein said photoelectric transducer means is so disposed so as to detect craterlike defects.

3. A method for inspecting surface defects of magnetic disks according to claim 1, wherein said photoelectric transducer means includes said photoelectric transducer element and a cylindrical lens arranged behind said stray-light-stop optical means and wherein said photoelectric transducer means is so disposed so as to detect stripe defects.

4. A method for inspecting surface defects of magnetic disks according to claim 1, wherein said photoelectric transducer means includes said photoelectric transducer element in addition to said stray-light-stop optical means, and stray-light-stop optical means includes said at least two plates with said apertures in the form of pinholes, and wherein said photoelectric transducer means is so disposed as to detect craterlike defects or stripe defects.

5. A method for inspecting surface defects of magnetic disks according to claim 1, wherein said stray-light-stop optical means includes said at least two plates with said apertures in the form of slits and wherein said photoelectric transducer means includes a cylindrical lens and said photoelectric transducer element behind said stray-light-stop optical means, and said photoelectric transducer means is so disposed as to detect strip defects.

6. A method for inspecting surface defects of magnetic disks according to claim 1, wherein said stray-light-stop optical means includes two convex lenses and one of said plates with said aperture in the form of a pinhole inserted between said convex lens.

7. A method for inspecting surface defects of magnetic disks according to claim 6, wherein said photoelectric transducer means includes a cylindrical lens inserted between said stray-light-stop optical means and another of said two plates.

8. A method for inspecting surface defects of magnetic disks according to claim 1, wherein said stray-light-stop optical means includes two of said plates having said apertures therein.

9. A method for inspecting surface defects of magnetic disks according to claim 8, wherein said photoelectric transducer means includes a cylindrical lens and a third plate having an aperture therein, said cylindrical lens being arranged between said stray-light-stop optical means and said third plate.

10. An apparatus for inspecting surface defects of magnetic disks comprising:

a parallel coherent oblique illumination unit;

a photoelectric transducer unit having a stray-light-stop optical system, scattered beams being cut off by said stray-light-stop optical system, said photoelectric unit including a photoelectric transducer element and at least two plates, each plate having an aperture therein for enabling introduction of light beams to said photoelectric transducer unit; and a sample feeding stage.

11. An apparatus for inspecting surface defects of magnetic disks according to claim 10, wherein said stray-light-stop optical system includes two convex lenses and one of said plates with said aperture in the form of a pinhole inserted between said convex lenses.

12. An apparatus for inspecting surface defects of magnetic disks according to claim 11, wherein said photoelectric transducer unit includes a cylindrical lens and another of said plates having said aperture, said cylindrical lens being arranged between said stray-light-stop optical system and said another of said plates.

13. An apparatus for inspecting surface defects of magnetic disks according to claim 10, wherein said photoelectric transducer unit includes said photoelectric transducer element and one of said plates with said aperture in the form of a pinhole arranged behind said stray-light-stop optical system.

14. An apparatus for inspecting surface defects of magnetic disks according to claim 10, wherein said photoelectric transducer unit includes said photoelectric transducer element and a cylindrical lens arranged behind said stray-light-stop optical system.

15. An apparatus for inspecting surface defects of magnetic disks according to claim 10, wherein said stray-light-stop optical system includes two of said plates having said apertures therein.

16. An apparatus for inspecting surface defects of magnetic disks according to claim 15, wherein said photoelectric transducer unit includes a cylindrical lens and another of said plates having an aperture therein, said cylindrical lens being arranged between said stray-light-stop optical system and said another of said plates.

17. An apparatus for inspecting surface defects of magnetic disks comprising:
   a coherent oblique illuminating unit which illuminates substantially in a parallel beam;
   a photoelectric transducer unit having a stray-light-stop optical system, scattered beams being cut off by said stray-light-stop optical system, said photoelectric transducer unit including a cylindrical lens and a photoelectric transducer element behind said stray-light-stop optical system; and
   a sample feeding stage.

18. An apparatus for inspecting surface defects of magnetic disks according to claim 17, wherein said stray-light-stop optical system includes a plurality of plates having pinholes.

19. An apparatus for inspecting surface defects of magnetic disks according to claim 17, wherein said stray-light-stop optical system includes a plurality of plates having slits.

* * * * *